United States Patent [19]
DiTraglia

[11] Patent Number: 4,822,336
[45] Date of Patent: Apr. 18, 1989

[54] BLOOD GLUCOSE LEVEL SENSING

[76] Inventor: John DiTraglia, 3317 Orchard Dr., Portsmouth, Ohio 45662

[21] Appl. No.: 164,473

[22] Filed: Mar. 4, 1988

[51] Int. Cl.$^4$ ............................................. A61M 5/00
[52] U.S. Cl. ...................................... 604/50; 604/66; 604/67; 128/635; 204/403; 204/415
[58] Field of Search ............................ 604/50, 65-67; 128/632, 635; 204/415, 403, 1 K

[56] References Cited

U.S. PATENT DOCUMENTS

| | | | |
|---|---|---|---|
| 3,837,339 | 9/1974 | Aisenberg et al. | 604/66 |
| 4,055,175 | 10/1977 | Clemens et al. | 604/66 |
| 4,538,616 | 9/1985 | Rogoff | 128/632 |
| 4,596,575 | 6/1986 | Rosenberg et al. | 604/891.1 |
| 4,679,562 | 7/1987 | Kuksha | 128/635 |
| 4,759,828 | 7/1988 | Young et al. | 204/415 |

*Primary Examiner*—Stephen C. Pellegrino
*Attorney, Agent, or Firm*—Robert B. Watkins

[57] ABSTRACT

A method of sensing blood glucose levels in the steps of passing glucose from a peritoneal fluid through a semi-permeable membrane and into a closed chamber, metabolizing the passed glucose in the closed chamber with a yeast suspension to produce a level of carbon dioxide and detection of the level of carbon dioxide, and controlled insulin infusion into blood as a consequence of detected carbon dioxide level. Implantable apparatus is also provided for carrying out the method within a body of live tissue.

16 Claims, 1 Drawing Sheet

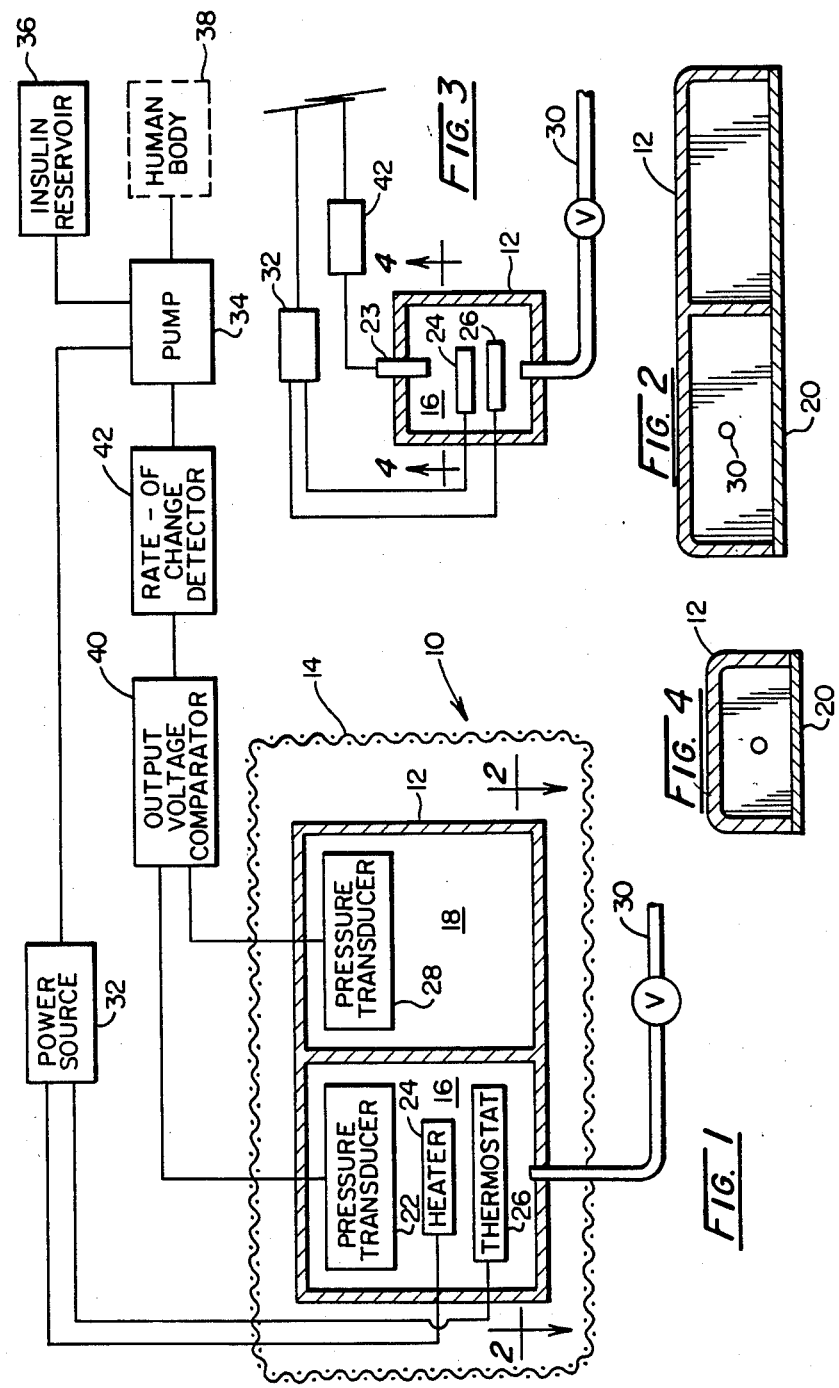

BLOOD GLUCOSE LEVEL SENSING

TECHNICAL FIELD

This invention relates generally to blood glucose level sensing, and particularly concerns both methods and apparatus useful for detecting blood glucose levels and controlling insulin infusion in the treatment of diabetes mellitus.

BACKGROUND OF THE INVENTION

An ideal blood glucose concentration level sensor capable of automatically directing or controlling the operation of an insulin infusion pump should be preferably in the form of a relative small assembly which may be easily implanted in a patient's body and which would be effective in operation and reliable over a long period of time.

Various prior art practioners have sought to provide a medically and commercially device, but there remains further room for improvement. As an example of this prior practice U.S. Pat. No. 4,679,562 Luksha discloses a glucose sensor which provides a detection mechanism adapted to determine glucose levels in blood either in-vivo or in-vitro applications. Enzyme films are described as encased in a silicone rubber film for implantation. Another U.S. Pat. No. 4,650,547 Gough relates to a method and membrane applicable to an implantable sensor. The membrane is disclosed as combination of a hydrophilic material and a hydrophobic material.

U.S. Pat. No. 4,596,575 Rosenberg et al. reveals a liquid delivery system useful as an implantable micropump for delivering insulin or other drugs. Another U.S. Pat. No. 4,557,726 Reinicke shows a pulsatile system and method in which medication is dispensed to the body during short dispensing periods separated by relatively long intervals between such dispensing periods.

U.S. Pat. No. 4,538,616 Rogoff discloses an implantable transducer capable of detecting variations in blood sugar levels by detecting changes in blood osmotic pressure. The transducer operates the insulin and/or glucose pumps which are said to be implanted. Still another U.S. Pat. No. 4,477,314 Richter et al., reveals an electrochemical method for determining glucose in a body fluid.

U.S. Pat. No. 4,366,033 Richter et al. relates to a method for determining the concentration of sugar using an electrocatalytic sugar sensor. A relatively impermeable diaphragm member is used in the process.

Also U.S. Pat. No. 3,837,339 Aisenberg et al. shows an implantable glucose monitor and alarm system for use in the measurement and control of blood glucose levels in diabetics.

Foreign Patent—Germany—DE No. 3228-551-A reveals a method using an electrocatalytic sensor having a measuring electrode fitted with a membrane of measuring glucose in body fluids.

Historically, patients suffering from diabetes have taken the responsibility of controlling their blood sugar level by injections of insulin either on a timely basis or on the basis of symptoms which they feel. Such methods are not exact and only responsive to secondary feelings rather than quantitative body functional measurements. For this reason they are relatively inexact and the control of the disease lacks the kind of controlled medication application which is desired. Consequentially the above patents are examples of the efforts of the medical community has expended to find a more exact and convenient method of providing the appropriate medication such as insulin and/or glucose as the need requires.

As revealed in the prior art patents, the basic components of such a system include a sensing subsystem for the detection of the blood glucose concentration level and another subsystem for providing the appropriate amount of glucose or insulin as needed. The latter subsystem has been developed and components such as pumps, batteries, catheters, and surgical procedures are available, although integrated into relatively complex total system apparatus.

In the sensing subsystem further simplification and increased accuracy in sensitivity are still sought after objectives.

The present invention provides a method and sensor assembly which utilizes as a principle of operation the detection of changes which result from the production of carbon dioxide by yeast in the metabolism of body glucose.

SUMMARY OF THE INVENTION

The method of the present invention basically involves the steps of passing glucose from a peritoneal fluid through a semi-permeable membrane and into a closed chamber, reacting or metabolizing the glucose in the closed chamber with a yeast suspension to form carbon dioxide and thereby increase the internal fluid pressure in the closed chamber, detecting the increased internal fluid pressure in the closed chamber or alternatively sensing carbon dioxide concentration levels in the chamber, and finally controlling insulin infusion into blood as a consequence of the detected carbon dioxide level or increased internal fluid pressure in an in-step manner.

From an apparatus standpoint the invention involves a closed chamber defined in part by a membrane that is permeable to glucose but impermeable to body cells, proteins, etc., a yeast in said closed chamber in suspension in a fluid that is isotonic as to peritoneal fluid, and carbon dioxide-sensing electrode means or pressure transducer means in the closed chamber and connected to insulin infusion control equipment. In the practice of the invention the level of carbon dioxide in the closed chamber correlates to a level of glucose in the patient's blood.

The foregoing and other advantages of the invention will become apparent from the following disclosure in which a preferred embodiment of the invention is described in detail and illustrated in the accompanying drawings. It is contemplated that variations in structural features and arrangement of parts may appear to the person skilled in the art, without departing from the scope or sacrificing any of the advantages of the invention.

BRIEF DESCRIPTION OF THE DRAWINGS

FIG. 1 is a schematic representation, partially in elevation, of a preferred embodiment of the apparatus of this invention; and FIG. 2 is a cross sectional view taken at line 2—2 of FIG. 1.

FIG. 3 is a schematic representation, partially in elevation of another embodiment of the apparatus of this invention; and FIG. 4 is a cross sectional view taken at the line 4—4 of FIG. 3.

DETAILED DESCRIPTION OF THE INVENTION AND BEST MODE FOR CARRYING OUT THE PREFERRED EMBODIMENT

Referring to the drawings, FIG. 1 schematically illustrates a preferred embodiment of an implant assembly 10 constructed in accordance with the present invention. Assembly 10 is preferably miniaturized and includes a pre-formed housing 12 which is placed within pressure screen 14. The assembly 10 is constructed to be implantable in live human or animal tissue by surgical procedures that are well known in medical practice. The pressure screen may be any suitable rigid material capable of withstanding forces from nearby body organs.

Also, housing 12 contains a first closed chamber 16 and a second closed chamber 18. Such chambers are each partially defined by a semipermeable membrane designated 20 (FIG. 2). Membrane 20 is permeable as to glucose but impermeable as to body cells, large molecules (proteins), and the like.

A first chamber 16 contains a miniaturized first pressure transducer 22, a sheathed resistance heater 24, and a thermostatic temperature sensing device 26. Device 26 preferably controls the temperature in chamber 16 to a temperature above 98.6° F., and to as high as about 106° F. The second closed chamber 18 contains a second miniaturized pressure transducer designated 28. A valved inlet tube 30 cooperates with the first closed chamber 16 and is used for introducing a yeast suspension into chamber 16 for use in the system's reaction with or metabolism of body glucose.

Cooperating with the implant assembly 10 is the power source 32 such as a battery that connects to a heater means 24, thermostat means 24, and insulin infusion pump means 34. Pump 34, when actuated, pumps insulin from the reservoir 36 into the patient's bloodstream. Also included in the practice of this invention is the electronics comparator 40 which receives the output voltages from pressure transducers 22 and 28. The difference voltage is detected by comparator 40 and is provided as an input to the rate-of-change detector 42 which differentiates the input signal to determine the rate of change of pressure difference between pressure transducers 22 and 28. The rate of change detector 42 may be of the conventional type.

In operation of the invention, a baker's or brewer's yeast suspension, preferably in a fluid that is isotonic as to peritoneal fluid, is introduced into closed chamber 16. Glucose contained within the peritoneal fluid passes and equilibrates through semi-permeable membrane 20 into chamber 16 and reacts with the yeast/isotonic fluid suspension to produce carbon dioxide at a rate which varies according to the concentration of glucose in the blood. The rate of change in produced carbon dioxide correlates with changes in the level of glucose in the patient's bloodstream and causes pressure transducer 22 to provide a first output signal to voltage comparator 40. Transducer 28 provides a second output signal that is representative of the pressure in chamber 18. Similarly, any increase in pressures occurring within the peritoneal fluid as a result of patient movement, positioning, etc. are transmitted equally to both pressure transducers 22 and 28. The difference between the output of both pressure transducers is detected at the comparator 40 and represents the true increase in pressure in chamber 16 due to carbon dioxide production. The rate of change detector 42 determines the degree of $CO_2$ production activity occurring within chamber 16 and produces an output signal that is useful for the control of insulin infusion pump 34.

Alternatively, this invention includes the use of a conventional carbon dioxide-responsive electrode means 23 instead of the use of a miniaturized fluid pressure transducer means 22. Such device 23 senses the level of carbon dioxide production in the first closed chamber means 16 and it utilized to regulate or control the operation of the system insulin infusion pump 34. When this electrode sensing device is incorporated into the invention it becomes unnecessary to utilize the second closed chamber 18, second fluid pressure transducer 28, and comparator means 40. See FIG. 3. Also, use of the pressure screen 14 becomes unnecessary in this apparatus configuration.

It is herein understood that although the present invention has been specifically disclosed with the preferred embodiment and examples, modification and variation of the concepts herein disclosed may be resorted to by those skilled in the art. Such modifications and variations are considered to be within the scope of the invention and the appended claims.

I claim:

1. In a method of sensing blood glucose levels within a body of live tissue having peritoneal fluid therein for the control of insulin infusion into the body, the steps of:
    (a) passing glucose from the peritoneal fluid through a semipermeable membrane and into a closed chamber;
    (b) reacting the glucose passed into said closed chamber with a yeast suspension within the chamber to produce a level of carbon dioxide in said closed chamber;
    (c) detecting the level of carbon dioxide in said closed chamber; and
    (d) controlling insulin infusion into blood as a consequence of the detected carbon dioxide level.

2. The method defined by claim 1 wherein said reaction step is accomplished at temperature of about 106° F.

3. In a method of sensing blood glucose levels within a body of live tissue having peritoneal fluid therein for the control of insulin infusion into the body, the steps of:
    (a) passing glucose from the peritoneal fluid through a semipermeable membrane and into a closed chamber;
    (b) reacting the glucose passed into said closed chamber with a yeast suspension to form carbon dioxide and to increase the internal fluid pressure in said closed chamber;
    (c) detecting the rate of internal fluid pressure increase in said closed chamber; and
    (d) controlling insulin infusion into blood as a consequence of the detected rate of internal fluid pressure increase.

4. The method defined by claim 3 wherein said reaction is accomplished at a temperature of about 106° F.

5. Apparatus for implantation into a human body to sense blood glucose levels for the control of insulin infusion into the blood, comprising:
    (a) a closed chamber defined in part by a membrane that is permeable to glucose;
    (b) a yeast in said closed chamber in suspension in a fluid isotonic as to peritoneal fluid; and (c) carbon dioxide-responsive means in said closed chamber and connected to insulin infusion control equipment, said carbon dioxide-responsive means sensing a closed chamber condition that correlates to a level of blood glucose.

6. The apparatus defined by claim 5 wherein said carbon dioxide-responsive means is a carbon dioxide-sensitive electrode.

7. The apparatus defined by claim 5 wherein said carbon dioxide-responsive means is a fluid pressure transducer means.

8. The apparatus defined by claim 7 and further comprising a rigid screen means, said screen means encasing said closed chamber and being permeable to peritoneal fluid.

9. The apparatus defined by claim 7 and further comprising a second closed chamber in part defined by a membrane, a fluid isotonic as to peritoneal fluid in said second closed chamber, second pressure transducer means in said second closed chamber means, and comparator means, said comparator means receiving the output signals of said first and second pressure transducer means and producing an output signal that regulates the insulin infusion control equipment in response to the pressure difference between said first and second pressure transducer means.

10. The apparatus defined by claim 9 and further comprising a rigid screen means, said rigid screen means encasing said first and second closed chambers and being permeable to peritoneal fluid.

11. The apparatus defined by claim 9 and further comprising heater means in said first closed chamber, said heater means heating said yeast and isotonic fluid suspension to a temperature greater than 98.6° F.

12. The apparatus defined by claim 11 and further comprising thermostatic control means, said thermostatic control means controlling said heater means and said yeast and isotonic fluid suspension in said first closed chamber to a temperature of about 106° F.

13. The apparatus defined by claim 9 and further comprising a fluid pressure rate of change detector, said fluid pressure rate of change detector receiving the output of said comparator means and producing an output signal that regulates the insulin infusion control equipment in response to the rate of change of pressure difference between said first and second pressure transducer means.

14. The apparatus defined by claim 5 and further comprising heater means in said closed chamber, said heater means heating said yeast and isotonic fluid suspension to a temperature greater than 98.6° F.

15. The apparatus defined by claim 9 and further comprising thermostatic control means, said thermostatic control means controlling said heater means and said glucose and isotonic fluid suspension to a temperature of about 106° F.

16. The apparatus defined by claim 5 and further comprising a rate of change detector means, said rate of change detector means receiving the output of said carbon dioxide-responsive means and regulating the insulin infusion control equipment in response to the change in level of carbon dioxide sensed by said carbon dioxide-responsive means.

* * * * *